United States Patent [19]

Kardouche et al.

[11] Patent Number: 5,601,837
[45] Date of Patent: Feb. 11, 1997

[54] PSYLLIUM CHOLESTYRAMINE COMPOSITIONS WITH IMPROVED PALATABILITY

[75] Inventors: Nabil G. Kardouche, Loveland; John A. Colliopoulos, Cinicinnati, both of Ohio

[73] Assignee: The Procter & Gamble Company, Cincinnati, Ohio

[21] Appl. No.: 460,028

[22] Filed: Jun. 2, 1995

Related U.S. Application Data

[63] Continuation of Ser. No. 278,707, Jul. 22, 1994, abandoned, which is a continuation of Ser. No. 113,560, Aug. 27, 1993, abandoned, which is a continuation of Ser. No. 895,194, Jun. 5, 1992, abandoned, which is a continuation of Ser. No. 630,595, Dec. 20, 1990, abandoned.

[51] Int. Cl.$^6$ ............................................. A61K 31/785
[52] U.S. Cl. .................... 424/439; 424/78.1; 424/78.01; 424/489
[58] Field of Search ................................ 424/439, 489, 424/78.01, 78.1

[56] References Cited

U.S. PATENT DOCUMENTS

| | | | |
|---|---|---|---|
| 3,148,114 | 9/1964 | Fahrenbach et al. | 167/55 |
| 3,499,960 | 3/1970 | Macek et al. | 424/33 |
| 3,923,972 | 12/1975 | Fields et al. | 424/78 |
| 3,974,272 | 8/1976 | Polli et al. | 424/78 |
| 4,321,263 | 3/1982 | Powell et al. | 424/195 |
| 4,459,280 | 7/1984 | Colliopoulos et al. | 424/35 |
| 4,511,561 | 4/1985 | Maddaus et al. | 424/195.1 |
| 4,548,806 | 10/1985 | Colliopoulos et al. | 424/35 |
| 4,565,702 | 1/1986 | Morley et al. | 426/93 |
| 4,619,831 | 10/1986 | Sharma | 426/93 |
| 4,747,881 | 5/1988 | Shaw et al. | 106/209 |
| 4,778,676 | 10/1988 | Yang et al. | 424/78.01 |
| 4,790,991 | 12/1988 | Shaw et al. | 424/441 |
| 4,818,539 | 4/1989 | Shaw et al. | 424/441 |
| 4,824,672 | 4/1989 | Day et al. | 424/195.1 |
| 4,828,842 | 5/1989 | Furst et al. | 424/480 |
| 4,843,098 | 6/1989 | Shaw et al. | 514/778 |
| 4,849,222 | 7/1989 | Broaddus | 424/195.1 |
| 4,882,157 | 11/1989 | Yang et al. | 424/440 |
| 4,883,788 | 11/1989 | Day et al. | 514/57 |
| 4,895,723 | 1/1990 | Amer et al. | 424/79 |
| 4,950,689 | 8/1990 | Yang et al. | 514/777 |
| 4,996,051 | 2/1991 | Meer et al. | 424/195.1 |
| 5,009,916 | 4/1991 | Colliopoulos et al. | 426/615 |
| 5,023,245 | 6/1991 | Kuhrts | 514/54 |
| 5,048,760 | 9/1991 | Barbera et al. | 241/9 |
| 5,422,101 | 6/1995 | Daggy et al. | 424/78.01 |

FOREIGN PATENT DOCUMENTS

| | | |
|---|---|---|
| 0323666 | 12/1989 | European Pat. Off. |
| 362926 | 4/1990 | European Pat. Off. |
| 387933 | 9/1990 | European Pat. Off. |
| 6888M | 6/1969 | France |
| 249634 | 9/1987 | German Dem. Rep. |
| 1446352 | 8/1976 | United Kingdom |
| 80/00658 | 4/1980 | WIPO |
| 144644 | 6/1985 | WIPO |

OTHER PUBLICATIONS

Anderson et al., "Hypocholesterolemic Effects of Psyllium Mucilloid for Hypercholesterolemic Men", Fed. Proceed., 46 (3), p. 877 (1987).

Anderson et al. "Dietary Fiber: Hyperlipidemia, Hypertension and Coronary Disease", Amer. J. Gastroent., 81, pp. 907–919 (1986).

Fagerberg, "The Effects of a Bulk Laxative (Metamucil®) on Fasting Blood Glucose, Serum Lipids and Other Variables in Constipated Patients with Non–Insulin Dependent Adult Diabetes", Curr. Thera. Res., vol. 31 (2), pp. 166–172 (1982).

Forman et al., "Increased Excretion of Fecal Bile Acids by an Oral Hydrophilic Colloid", Proc. Soc. Exp. Biol. Med. vol. 120(3), pp. 1060–1063 (1968).

Beher et al., "The Effect of Psyllium Hydrocolloid and Cholestyramine on Hepatic Bile Lipid Composition in Man", Henry Ford Hospital Medical Journal, 21(1), pp. 21–30 (1973).

Merck Index, 10th Edition, Merck & Co. Inc. (1983), No. 2182: "Cholestyrramine Resin".

Stein, "Management of Hypercholesterolemia, Approach to Diet and Drug Therapy", The Americal Journal of Medicine, vol. 87 (4A), pp. 20S–27S (1989).

Questran® (Bristol–Myers) and Cholybars® (Parke Davis), Physicians Desk Reference, 44th Edition, pp. 726–729 and 1595–1597 (1990).

Metamucil®, Physician's Desk Reference for Non–Prescription Drugs, 9th Edition (1988), Medical Economics Company, Inc., pp. 642–644.

*Primary Examiner*—Raj Bawa
*Attorney, Agent, or Firm*—Mary Catherine Poland; Douglas C. Mohl; Kim William Zerby

[57] ABSTRACT

This invention relates to an oral pharmaceutical composition comprising from about 1% to 75%, by weight, psyllium husk with more than about 97% of the psyllium husk being smaller than about 100 mesh screen; from about 1% to 65%, by weight, cholestyramine; and wherein the ratio of the psyllium husk to the cholestyramine is from about 3:1 to about 1:2, and wherein the composition delivers from 1 g to 30 g of the psyllium husk and from about 4 g to about 30 g of the cholestyramine daily when the composition is taken orally in one or more doses.

10 Claims, No Drawings

PSYLLIUM CHOLESTYRAMINE COMPOSITIONS WITH IMPROVED PALATABILITY

This is a continuation of application Ser. No. 08/278,707 filed on Jul. 22, 1994, now abandoned which is a continuation of application Ser. No. 08/113,560 filed on Aug. 27, 1993 now abandoned, which is a continuation of application Ser. No. 07/895,194 filed on Jun. 5, 1992 now abandoned, which is a continuation of application Ser. No. 07/630,595 filed Dec. 20, 1990 now abandoned.

BACKGROUND

This invention relates to pharmaceutical compositions comprising small particle size (smaller than about 80 mesh U.S. standard) psyllium husk and cholestyramine having improved cholestyramine aesthetics, and a method for treating hypercholesterolemia by administering said pharmaceutical composition.

High blood cholesterol levels are associated with life threatening cardiac diseases. A drug of choice in the treatment of such disorders is cholestyramine resin, which is known as a basic anion exchange resin. Cholestyramine helps to lower blood cholesterol levels apparently by binding to bile acids in the intestine. It is believed that this in turn causes an increase in hepatic metabolism of cholesterol to replenish the bile acids lost to complexation with the cholestyramine.

Cholestyramine is usually dosed using from four to thirty-two grams, given once daily or divided into two, three, or four equal intervals. At the present time a commercial cholestyramine product, Questran® (manufactured by the Mead Johnson division of Bristol-Myers Company) is sold in a four grams unit dose powder packet or in bulk powder, and as Cholybars manufactured by Parke Davis) wherein one chewable bar contains four grams of cholestyramine. [*Physicians Desk Reference*, 44th Edition, pages 726–729 and 1595–1597 (1990).]

While the benefits of cholestyramine are well known and appreciated, the aesthetics (e.g., mouthfeel; taste; throat sticking) are considered by many users of cholestyramine to be very unpleasant. Obviously, poor aesthetics raise concern about how closely patients comply with any treatment regimen using cholestyramine. The unpleasant mouthfeel of cholestyramine is frequently described as a sandy, gritty texture which tends to stick to the back of the mouth and throat upon ingestion and which leaves an unpleasant fishy taste in the mouth.

Several attempts have been made to improve the palatability of cholestyramine. Patents which disclose such attempts include: East German Patent DD 249,634 published Sep. 16, 1987 by V&B Chemukombinat Bitterfeld (discloses grinding a basic anionic exchanger such as cholestyramine in a wet state and spraying on an aqueous solution of pectin during drying); Great Britain Patent Specification Number 1,446,352, published Aug. 18, 1976 by Merck & Co., Inc. (discloses an oral pharmaceutical composition in liquid form comprising a coacervate of a hydrophilic colloid of a cellulose derivative, such as sodium carboxymethyl cellulose, and cholestyramine); French Medical Patent 6,888 M published Jun. 4, 1964 by Mead Johnson & Company (discloses dry mixing acacia gum with cholestyramine resin to aid in making the extreme astringency of cholestyramine disappear); U.S. Pat. No. 4,895,723, issued to Amer et al. Jan. 23, 1990 (describes orally ingestible compositions for reduction of blood cholesterol levels comprising cholestyramine and a water-soluble carbohydrate syrup such as high fructose corn syrup or a liquid alcohol polyol humectant such as glycerine); U.S. Pat. No. 4,843,098, issued to Shaw et al. Jun. 27, 1989, U.S. Pat. No. 4,818,539, issued to Shaw et al. Apr. 4, 1989, and U.S. Pat. No. 4,790,991, issued to Shaw et al. Dec. 13, 1989, divisions of U.S. Pat. No. 4,747,881, issued to Shaw et al. May 31, 1988 (relating to preswelled substantially anhydrous hydrocolloid aggregate such as carboxymethyl cellulose with a size range of about 4 to about 70 U.S. mesh, and a substrate comprising dietary fiber and/or drug, such as cholestyramine); U.S. Pat. No. 4,778,676, issued to Yang et al. Oct. 18, 1988 (discloses a chewable delivery system for actives comprising an active, such as cholestyramine, precoated with at least one material selected from the group consisting of lecithin, polyoxyalkenes having chain lengths of about four carbons or less, glycerides having a melting point of 100° C. or less, polyalkylene glycols having a molecular weight of 3,700 or less, synthetic and natural waxes and mixtures thereof, and a confectionery matrix comprising a binder system of gelatin and a humectant material); U.S. Pat. No. 3,974,272, issued to Pollt et al. Aug. 10, 1976 (discloses a palatable oral coacervate composition containing cholestyramine and a Modified Gum selected from the group consisting of hydrophillic colloid of cellulosive material and charged anionic gum in an aqueous medium); and U.S. Pat. No. 3,499,960, issued to Macek et al. (discloses coating the cholestyramine particles with an acrylic polymer crosslinked with allylsucrose).

Other publications relating to therapeutic use of cholestyramine or psyllium include the following. European Patent Application Publication No. 323,666, published Jul. 12, 1989 by The Procter & Gamble Company. This patent describes methods and compositions for reducing blood cholesterol levels by oral administration of psyllium and cholestyramine, optionally in combination with polyol polyesters. It is also stated therein that "cholestyramine resin, administered orally, has sometimes been associated with constipation and preparations containing cholestyramine often have an unpleasant sandy or gritty quality. Advantageously, these problems associated with cholestyramine are alleviated when the psyllium and/or psyllium plus optional polyol polyesters are employed therewith."

U.S. Pat. No. 4,824,672, issued to Day et al. Apr. 25, 1989, discloses an orally utilizable pharmaceutical composition comprising gel-forming fiber (such as guar gum, psyllium seed, pectin, glucomannan, oat and barley) and a mineral salt (such as calcium carbonate, magnesium carbonate, or potassium carbonate) said to be administered to humans to reduce serum cholesterol levels.

*Management of Hypercholesterolemia, Approach to Diet and Drug Therapy*, Stein, The American Journal of Medicine, Vol. 87(4A) (1989) advises patients who experience constipation from the use of cholestyramine or colestipol (bile acid sequestrants used to decrease blood cholesterol levels) to take a bulk laxative, such as psyllium fiber, with the evening dose of sequestrant if other dietary changes do not alleviate the problem of constipation.

*The Effect of Psyllium Hydrocolloid and Cholestyramine on Hepatic Bile Lipid Composition in Man*, Behrer et al., Henry Ford Hospital Medical Journal, Vol. 21(1) (1973), examined the effects of psyllium hydrocolloid and of cholestryamine on the total cholesterol, total phospholipid, total bile salt, cholate, chenodeoxycholate, and deoxycholate concentrations of 6 post-cholecystectomy patients.

Although there has been much research devoted to cholestyramine and to improving the aesthetics of cholestyramine, there continues to be a need for improved products containing cholestyramine. In the present invention, it has surprisingly been discovered that small particle size psyllium husk, smaller than that previously commercially available in certain laxative products, when used in combination with cholestyramine, improves the aesthetics of the cholestyramine. The object of the present invention is therefore to provide a pharmaceutical composition comprising small particle size psyllium husk and cholestyramine with improved aesthetics, including palatability and/or mouthfeel. A further object of this invention is to provide a method for improving the palatability and overall mouthfeel of cholestyramine and a method for enhancing compliance and convenience with a treatment regimen for treating hypercholesterolemia by administering to humans a pharmaceutical composition comprising small particle size psyllium husk and cholestyramine. An object of the present invention is also to provide a method for treating hypercholesterolemia by administering to humans a pharmaceutical composition comprising small particle size psyllium husk and cholestyramine. Another object of the present invention is to provide a bowel normalizing benefit to patients being treated for hypercholesterolemia through administration of a pharmaceutical composition comprising small particle size psyllium husk and cholestyramine.

These and other objects of the present invention will become readily apparent from the detailed description which follows.

All percentages and ratios used herein are by weight and all measurements are made at 25° C. unless otherwise specified. Screen mesh sizes used herein are based on U.S. standards.

SUMMARY OF THE INVENTION

The present invention relates to a pharmaceutical composition comprising: (a) cholestyramine; and (b) small particle size psyllium husk (i.e., smaller than about 80 mesh screen) wherein the ratio of small particle size psyllium husk to cholestyramine is from about 3:1 to about 1:2.

The present invention further relates to a method for improving the aesthetics of cholestyramine, said method comprising mixing cholestyramine with small particle size psyllium husk in a liquid in a ratio of small particle size psyllium husk to cholestyramine from about 3:1 to about 1:2.

Additionally the present invention relates to a method for treating hypercholesterolemia in humans, said method comprising administering to a human in need of such treatment a safe and effective amount of a pharmaceutical composition according to the present invention.

DETAILED DESCRIPTION OF THE INVENTION

Pharmaceutical Compositions

It has been surprisingly discovered that combining small particle size psyllium husk with cholestyramine greatly reduces the unpleasant aesthetics of the cholestyramine resin, even relative to aesthetically improved compositions comprising cholestyramine and the larger particle size psyllium husk (commercially available, e.g., Metamucil®, sold by The Procter & Gamble Company) taught for use by European Patent Application Publication No. 323,666, published Jul. 12, 1989 by The Procter & Gamble Company.

Combination of the small particle size psyllium husk with the cholestyramine may be accomplished through simple admixture (e.g., by a dry blending process), by preferably forming a dry drink mix composition or by admixing in a liquid (e.g., water) a composition comprising small particle size psyllium husk and a composition comprising cholestyramine, as described in greater detail hereinafter.

A. Small Particle Size psyllium Husk.

The small particle size psyllium husk used in the present invention is from psyllium seeds, from plants of the Plantago genus. Various species such as *Plantago lanceolate, P. rugelii,* and *P. major* are known. Commercial psyllium husk include the French (black; *Plantago indica*), Spanish (*P. psyllium*) and Indian (blonde; *P. ovata*). Indian (blonde) psyllium husk is preferred for use herein. Also preferred is psyllium husk which is at least about 85% pure, more preferably at least about 90% pure, and most preferably at least about 95% pure.

The psyllium husk is obtained from the seed coat of psyllium seed. It is typical to remove the seed coat from the rest of the seed by, for example, slight mechanical pressure, and then to use only the seed coat. The seed coat is preferably removed and sanitized by methods known in the art (e.g., ethylene oxide sanitization or superheated steam sanitization as taught in European Patent Application Publication No. 308,003, published Mar. 22, 1989 by The Procter & Gamble Company the disclosures of which are incorporated herein by reference in their entirety) prior to reducing the particle size to that described herein. Methods for reducing psyllium particle size to those of the present invention are known in the art, preferably may be reduced by the use of a stud mill (also known as "pin mills") under conditions which selectively reduce the psyllium husk size relative to non-husk impurity, thereby allowing for further purification if so desired, as described in more detail in European Patent Application Number 362,926, published Apr. 11, 1990 by The Procter & Gamble Company.

"Small particle size psyllium husk", as used herein, means that essentially all of the psyllium husk is smaller than about 80 mesh screen. The preferred particle size comprises small particle psyllium husk wherein more than about 97% are smaller than about 100 mesh and less than about 40% are smaller than about 200 mesh. Particle sizes may be readily determined by one of ordinary skill in the art, for example by sieving using an Alpine Laboratory Air Jet Sieve, Type 200 LS (sold by Alpine American Corporation, Natick, Mass.).

While not essential, it is preferred that the small particle size psyllium used in the present invention be agglomerated and more preferably these agglomerates also comprise the cholestyramine. Agglomerated psyllium is well known. Agglomerating psyllium husk appears to improve the mixability and suspendability of the small size particle psyllium husk in liquids, especially water. Agglomeration processes may be chosen by one of ordinary skill in the art as appropriate for the small particle size psyllium husk, in the present invention. An example of a fluid bed agglomerating equipment useful in the agglomeration process is the Fluid Air, Inc., Model 0300 Granulator-Dryer.

The small particle size psyllium husk in the present invention comprises from about 1% to about 75% by weight of the pharmaceutical composition of the present invention and more preferably from about 10% to about 65%. Most preferred is that the small size psyllium husk comprises from about 30% to about 65% by weight of the pharmaceutical composition of the present invention. The ratio of small particle size psyllium husk to cholestyramine is from about 3:1 to about 1:2, preferably from about 2:1 to about 1:1.

B. Cholestyramine

The cholestyramine resin used in the present invention is a strongly basic anion exchange resin which contains quaternary ammonium functional groups attached to a styrene-divinylbenzene copolymer. [*The Merck Index,* 10th Edition, published by Merck & Co., No. 2182 (1983)]. Cholestyramine resin-containing compositions are available commercially in powder form under the tradenames Cuemid® (Merck, Sharp & Dome) and Questran® (Bristol Myers division of Mead Johnson). Cholestyramine is commercially available as Duolite AP-143 resin (Rohm & Haas Co.).

The cholestyramine resin in the present invention comprises from about 1% to about 65% by weight of the pharmaceutical composition of the present invention, and more preferably from about 10% to about 50%. Most preferred is that the cholestyramine resin in the present invention comprises from about 25% to about 50% by weight of the pharmaceutical composition of the present invention.

C. Optional Components:

The compositions of the present invention also optionally comprise food grade carrier materials suitable for human consumption. The carrier materials useful in the present invention include the group consisting of flavoring agents, sweetening agents, agglomerating agents (such as maltodextrin) and/or coloring agents.

Flavoring agents if optionally chosen may include certain volatile oils, liquids or dry agents which are pharmaceutically acceptable for internal ingestion by humans. Examples of such flavoring agents include citrus flavors (such as orange and grapefruit), strawberry, and cherry flavors.

Another optional component of the present invention, as noted above, is a sweetening agent. Examples of suitable sweetening agents include but are not limited to, saccharides, disaccharides and polysaccharides such as xylose, ribose, glucose, mannose, galactose, fructose, dextrose, sucrose, maltose, partially hydrolyzed starch, or corn syrup solids and sugar alcohols. Additionally low caloric sweetening agents may be used in the present invention, including, but not limited to, aspartame, saccharin, cyclamate, acesulfame (American Hoechst), gem sweet (Cumberland Packing Corp.), L-sugars (Lev-O-Cal Biospherics), Hernandulcin (University of Illinois), Alitame (Pfizer), Thaumatins, trichloro sucrose, Rebaudioside A, aspartyl-D-valine isopropyl ester, aspartyl amino malonates, dialkyl aspartyl aspartates, stevio side, glycyrrhizin, p-phenetylurea, 5-nitro-2-propoxy aniline and neohesperidin dihydrochalcone. Preferred artificial sweetners are saccharin, cyclamate, ausulfame K, and especially aspartame, sold as Nutrasweet® by G. D. Searle.

The food grade carrier materials comprise from about 0% to about 98% by weight of the pharmaceutical composition of the present invention, and more preferably from about 5% to about 80%. Most preferred is that the food grade carrier materials comprise from about 10% to about 50% by weight of the pharmaceutical composition of the present invention.

The combination in the present invention of small particle size psyllium husk and cholestyramine may be achieved by dry blending these materials by any means known to one skilled in the art, and preferably by a method which will achieve a uniform mix of the small particle size psyllium husk and cholestyramine. Examples of apparatuses which may be helpful in obtaining such uniformity are the Hobart mixer (model number N-50), the Glen mixer, and the Patterson-Kelly twin-shell blender.

Compositions of the present invention may also be formed into liquid suspensions (typically by the consumer just prior to ingestion) by mixing a composition comprising the small particle size psyllium husk with a composition comprising cholestyramine into a liquid, typically water. The present invention therefore also relates to methods for improving the aesthetics of cholestyramine by a method comprising mixing cholestyramine with small particle size psyllium husk in a liquid in a ratio of small particle size psyllium to cholestyramine from about 3:1 to about 1:2. Preferably, the pharmaceutical composition comprising the small particle size psyllium husk and cholestyramine or each component separately are dispersed in at least an eight ounce glass of water or fruit juices and drunk.

Method of Treatment

The method of treatment herein comprises orally administering to a patient in need of having a lowered blood cholesterol level a safe and effective amount of a mixture of small particle size psyllium husk and cholestyramine. The ratio of small particle size psyllium husk to cholestyramine should be from about 3:1 to about 1:2, and preferably from about 2:1 to about 1:1, wherein a patient in need of such treatment receives from 1 g to 30 g of the small particle size psyllium husk and from about 4 g to about 30 g of the cholestyramine daily. However, this can vary with size and condition of the patient and the patient's blood cholesterol levels. Such matters will, of course, be apparent to the attending physician. Furthermore, since the psyllium materials and cholestyramine are non-toxic, even higher ingestion levels can be used without undue side effects.

Treatment of the patient comprises continuous administration of small particle size psyllium husk and cholestyramine in order to lower and maintain low cholesterol levels. As used herein "continuous administration" means Ingestion by a human in need of said treatment one or more doses a day of small particle size psyllium and cholestyramine for two or more days. Daily ingestion of the present compositions preferably comprises from about 5 g to about 15 g of small particle size psyllium husk and from about 4 g to about 24 g of cholestyramine taken orally, with said ingestion being once daily or at two, three, or four regularly spaced intervals throughout the day. It may also be beneficial to administer said dose in relationship to meals, preferably prior to a meal, and at bedtime. It is essential to the present invention that the small particle size psyllium husk and cholestyramine be combined prior to administration. Preferably said materials, in powder form, are combined prior to use by a dry blending process, described in detail hereinabove, and then admixed with a liquid drink, preferably eight ounces, such as fruit juices and water, and drunk.

The following examples further describe and demonstrate embodiments within the scope of the present invention. The examples are given solely for the purpose of illustration and are not to be construed as limitations of the present invention as many variations thereof are possible without departing from the spirit and scope.

Example I

| Component | g/dose | % w/w |
|---|---|---|
| Small particle size psyllium mucilloid[a] | 3.400 g | 47.600 |
| Citric acid | 0.900 | 12.600 |
| Potassium citrate | 0.090 | 1.260 |
| Aspartame[b] | 0.060 | 0.840 |
| FD&C Yellow 6 | 0.0003 | 0.004 |
| D&C Yellow 10 | 0.001 | 0.014 |
| Artificial Grapefruit Flavor F57364/AP0551[c] | 0.011 | 0.154 |
| Naringin[d] | 0.011 | 0.154 |
| Cholestyramine resin[e] | 2.67 | 37.374 | a) The small particle size psyllium mucilloid is prepared and agglomerated by the following process: A psyllium-containing dry blend (85.42 parts by weight) comprising 62.96 parts by weight superheated steam sanitized psyllium husks (particle size of 98% minimum through 100 mesh screen) and 24.28 parts by weight Maltrin M100 (maltodextrin having a D. E. of about 10; sold by Grain Processing Corporation; Nuscatine, Iowa) is agglomerated by spraying the dry blend with a citric acid solution (11.83 parts by weight) comprising 3.64 parts by weight citric acid, and 8.19 parts by weight water using a Bepex Turboflex Model No. TFX-4 (sold by Bepex Corporation; Minneapolis, Minn.) and then drying using a six square foot bed stationary fluid bed dryer (sold by Bepex Corporation; Minneapolis, Minn.).
b) Nutrasweet® (G. D. Searle)
c) Firmenich, Inc. (Princeton, N.J.)
d) flavoring agent manufactured by Baromatic Corporation (Great Neck, N.Y.).
e) Duolite AP-143 resin (Rohm & Haas Co., Philadelphia, Pa.).

The process for manufacturing is as follows:

(1) Place the citric acid, potassium citrate, aspartame, FD&C yellow #6, D&C yellow #10, Artificial flavor F57364/AP0551, and Naringin in the bowl of a Hobart mixer (model number N-50).

(2) Mix for 5 minutes using speed #1.

(3) Add the small particle size psyllium mucilloid and mix for 5 minutes using speed #1.

(4) Add the cholestyramine resin and mix on speed #1 for 5 minutes or until a homogeneous mixture is obtained. A flavored small particle size psyllium/cholestyramine-containing drink, according to the present invention, is prepared by dispersing 7.143 grams of the above pharmaceutical composition according to the present invention, in 8 ounces of water which may then be drunk by a human in need of such treatment for hypercholesterolemia.

EXAMPLE II

| Component | grams/dose | % w/w |
| --- | --- | --- |
| Sugar Free Sunrise Smooth Metamucil ®, orange flavor[a] | 8.775 | 49.367 |
| Questran ®[b] | 9.000 | 50.633 |

[a] sold by The Procter & Gamble Co. (Cincinnati, Ohio) wherein 8.775 g of powder mix provides 5.1 g of small particle size psyllium 100% through 80 mesh screen.
[b] sold by The Bristol Myers division of Mead Johnson (Evansville, Indiana), wherein 9 g of powder mix provides 4.0 g of cholestyramine resin.

A patient in need of a cholesterol lowering agent may disperse 8.775 g of the Sugar Free Sunrise Smooth Metamucil®, orange flavor, and 9.0 g of Questran® into an eight ounce glass of water, stir the mixture to provide uniformity, and drink once every day or more according to their physician's orders.

A patient in need of 8 g of cholestyramine per day may combine 18.0 g of Questran® with 8.775 of Sugar Free Sunrise Smooth Metamucil®, orange flavor divided equally between two eight ounce glasses of water.

What we claim is:

1. An oral pharmaceutical composition comprising:
  (a) from about 1% to 75%, by weight, psyllium husk with more than about 97% of the psyllium husk being smaller than about 100 mesh screen;
  (b) from about 1% to 65%, by weight, cholestyramine; and wherein the ratio of the psyllium husk to the cholestyramine is from about 3:1 to about 1:2; and wherein the composition delivers from 1 g to 30 g of the psyllium husk and from about 4 g to about 30 g of the cholestyramine daily when the composition is taken orally in one or more doses.

2. An oral pharmaceutical composition according to claim 1, wherein the psyllium husk is agglomerated.

3. An oral pharmaceutical composition according to claim 1, wherein the psyllium husk is agglomerated and the agglomerates also comprise the cholestyramine.

4. An oral pharmaceutical composition according to claim 1, wherein the ratio of the psyllium husk to the cholestyramine is from about 2:1 to about 1:1.

5. An oral pharmaceutical composition according to claim 1 further comprising food grade carrier materials suitable for human consumption selected from the group consisting of flavoring agents, sweeteners, preservatives, coloring agents, binders, and combinations thereof.

6. An oral pharmaceutical composition comprising:
  (a) from about 10% to about 65%, by weight, psyllium husk having more than about 97% of the psyllium husk smaller than about 100 mesh screen;
  (b) from about 10% to about 50%, by weight, cholestyramine;
  (c) from about 5% to about 80%, by weight, food grade carrier materials suitable for human ingestion; and
  wherein the ratio of the psyllium husk to the cholestyramine is from about 2:1 to about 1:1; and wherein the composition delivers from 1 g to 30 g of the psyllium husk and from about 4 g to about 30 g of the cholestyramine daily when the composition is taken orally in one or more doses.

7. An oral pharmaceutical composition comprising:
  (a) from about 30% to about 65%, by weight, psyllium husk having more than about 97% of the psyllium husk smaller than about 100 mesh screen;
  (b) from about 25% to about 50%, by weight, cholestyramine;
  (c) from about 10% to about 50%, by weight, food grade carrier materials suitable for human ingestion; and
  wherein the ratio of the psyllium husk to the cholestyramine is from about 2:1 to about 1:1; and wherein the composition delivers from 1 g to 30 g of the psyllium husk and from about 4 g to about 30 g of the cholestyramine daily when the composition is taken orally in one or more doses.

8. A method for treating hypercholesterolemia in humans, the method comprising continuous administration to a human in need of such treatment of an oral pharmaceutical composition prepared according to claim 1, delivering from 1 g to 30 g of the psyllium husk and from about 4 g to about 30 g of the cholestyramine daily.

9. A method for treating hypercholesterolemia in humans, the method comprising continuous administration to a human in need of such treatment of an oral pharmaceutical composition prepared according to claim 3, delivering from 1 g to 30 g of the psyllium husk and from about 4 g to about 30 g of the cholestyramine daily.

10. A method for treating hypercholesterolemia in humans, the method comprising continuous administration to a human in need of such treatment of an oral pharmaceutical composition prepared according to claim 4, delivering from 1 g to 30 g of the psyllium husk and from about 4 g to about 30 g of the cholestyramine daily.

* * * * *